United States Patent
Duan et al.

(10) Patent No.: US 10,892,802 B2
(45) Date of Patent: *Jan. 12, 2021

(54) METAL PLATING COMPOSITIONS (71) Applicants: Dow Global technologies LLC, Midland, MI (US); Rohm and Haas Electronic Materials LLC, Marlborough, MA (US)

(72) Inventors: Lingli Duan, Shanghai (CN); Chen Chen, Shanghai (CN); Shaoguang Feng, Shanghai (CN); Zukhra I. Niazimbetova, Westborough, MA (US); Maria Anna Rzeznik, Shrewsbury, MA (US)

(73) Assignees: Rohm and Haas Electronic Materials LLC, Marlborough, MA (US); Dow Global Technologies LLC, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/603,319

(22) Filed: Oct. 7, 2019

(65) Prior Publication Data
US 2020/0031818 A1  Jan. 30, 2020

Related U.S. Application Data (62) Division of application No. 15/559,574, filed as application No. PCT/CN2015/077684 on Apr. 28, 2015, now Pat. No. 10,738,039.

(51) Int. Cl.

| | |
|---|---|
| H04B 7/0408 | (2017.01) |
| H04B 7/06 | (2006.01) |
| C07D 241/04 | (2006.01) |
| C07D 265/33 | (2006.01) |
| C07D 413/06 | (2006.01) |
| C07D 413/10 | (2006.01) |
| C07D 413/12 | (2006.01) |
| C08G 73/02 | (2006.01) |
| C08G 73/10 | (2006.01) |
| C09D 179/02 | (2006.01) |
| C09D 179/08 | (2006.01) |
| C25D 3/30 | (2006.01) |
| C25D 3/32 | (2006.01) |
| C25D 3/38 | (2006.01) |
| C25D 3/58 | (2006.01) |
| C25D 3/60 | (2006.01) |
| H04J 4/00 | (2006.01) |
| H04J 13/00 | (2011.01) |
| H04L 1/00 | (2006.01) |
| H04W 72/04 | (2009.01) |
| H04W 36/00 | (2009.01) |

(52) U.S. Cl.
CPC ......... *H04B 7/0408* (2013.01); *C07D 241/04* (2013.01); *C07D 265/33* (2013.01); *C07D 413/06* (2013.01); *C07D 413/10* (2013.01); *C07D 413/12* (2013.01); *C08G 73/028* (2013.01); *C08G 73/1017* (2013.01); *C09D 179/02* (2013.01); *C09D 179/08* (2013.01); *C25D 3/30* (2013.01); *C25D 3/32* (2013.01); *C25D 3/38* (2013.01); *C25D 3/58* (2013.01); *C25D 3/60* (2013.01); *H04B 7/0619* (2013.01); *H04B 7/0695* (2013.01); *H04B 7/0697* (2013.01); *H04J 4/00* (2013.01); *H04J 13/00* (2013.01); *H04L 1/0003* (2013.01); *H04W 72/042* (2013.01); *H04W 72/046* (2013.01); *H04W 72/0446* (2013.01); *H04W 72/0453* (2013.01); *H04W 36/0055* (2013.01); *H04W 36/0079* (2018.08)

(58) Field of Classification Search
CPC .. H04B 7/0408; C07D 265/33; C07D 241/04; C07D 413/06
USPC .................................................... 544/98, 106
See application file for complete search history.

(56) References Cited

U.S. PATENT DOCUMENTS

| | | | | |
|---|---|---|---|---|
| 10,106,512 B2 * | 10/2018 | Duan | ........................ | C25D 3/38 |
| 10,435,380 B2 * | 10/2019 | Duan | ........................ | C25D 3/38 |

FOREIGN PATENT DOCUMENTS

CN  101343361 B  * 12/2010

OTHER PUBLICATIONS

Search report for corresponding China Application No. 201580078702.4 dated Jul. 1. 2019.
Jin et al, "Synthesis of poly(crystine bisamide)-PEG block copolymers grafted with 1-(3-aminopropyl)imidazole and their phase transition behaviours", Polymers for Advanced Techologies, 2008, pp. 1558-1565, vol. 19.

(Continued)

*Primary Examiner* — Kahsay Habte
(74) *Attorney, Agent, or Firm* — John J. Piskorski (57) ABSTRACT

A method of providing spatial diversity for critical data delivery in a beamformed mmWave small cell is proposed. The proposed spatial diversity scheme offers duplicate or incremental data/signal transmission and reception by using multiple different beams for the same source and destination. The proposed spatial diversity scheme can be combined with other diversity schemes in time, frequency, and code, etc. for the same purpose. In addition, the proposed spatial diversity scheme combines the physical-layer resources associated with the beams with other resources of the same or different protocol layers. By spatial signaling repetition to avoid Radio Link Failure (RLF) and Handover Failure (HOF), mobility robustness can be enhanced. Mission-critical and/or time-critical data delivery can also be achieved without relying on retransmission.

1 Claim, 5 Drawing Sheets (56) References Cited

OTHER PUBLICATIONS

International search report for corresponding International Application No. PCT/CN2015/077684 dated Jan. 20, 2016.
Search report for corresponding European Application No. 15 89 0233 dated Oct. 16, 2018.

* cited by examiner

METAL PLATING COMPOSITIONS

The present application is a divisional application of application Ser. No. 15/559,574, filed Sep. 19, 2017.

FIELD OF THE INVENTION

The disclosed embodiments relate generally to wireless communication, and, more particularly, to spatial diversity scheme in a Millimeter Wave (mmW) beamforming system.

BACKGROUND

The bandwidth shortage increasingly experienced by mobile carriers has motivated the exploration of the underutilized Millimeter Wave (mmWave) frequency spectrum between 3G and 300G Hz for the next generation broadband cellular communication networks. The available spectrum of mmWave band is two hundred times greater than the conventional cellular system. The mmWave wireless network uses directional communications with narrow beams and can support multi-gigabit data rate. The underutilized bandwidth of the mmWave spectrum has wavelengths ranging from 1 mm to 100 mm. The very small wavelengths of the mmWave spectrum enable large number of miniaturized antennas to be placed in a small area. Such miniaturized antenna system can produce high beamforming gains through electrically steerable arrays generating directional transmissions.

Robust signaling and data forwarding in beamformed mmWave systems demands new design. Known issues including unreliable TX/RX paths, random radio link failure (RLF) and service interruption, and consequently the performance degradation particularly in mobility. For example, connection failure and slow handover (HO) may occur due to RLF. A radio link failure that occurs in the source network is likely to be caused by too late handover. Likewise, a radio link failure that occurs in the target network is likely to be cause by too early handover. HO to the wrong target network and unnecessary HO to another RAT may also occur.

The existing LTE mobility is complex but based on omni-directional antenna without beamforming. In general, LTE small cell mobility can be used as the baseline for a standalone mmWave small cell. However, the heavy reliance on directional transmissions and the vulnerability of the propagation environment present particular challenges arise from channel characteristics and beamforming in mmWave small cells. For example, directional antenna and beamforming makes signaling path and data path even less reliable than omni-directional systems because more intermittent links and limited wireless coverage need to be compensated. Multiple levels of beams, multiple beams per level, and multiple TDM beamformed control beams need to be tacked, switched, and aligned with, resulting in complex time-critical decision to tradeoff among robustness, spatial coverage, speed, and link budget. Furthermore, different spatial paths offered by different levels of dedicated and control beams result in different channel coherent time and fading dynamics. Multiple choices of spatial beams thus offer more spatial diversity to be explored in mmWave small cells.

A solution of achieving spatial diversity for enhancing the reliability and performance of data and control path in mmWave small cell system is sought.

SUMMARY

A method of providing spatial diversity for critical data delivery in a beamformed mmWave small cell is proposed. The proposed spatial diversity scheme offers duplicate or incremental data/signal transmission and reception by using multiple different beams for the same source and destination. The proposed spatial diversity scheme can be combined with other diversity schemes in time, frequency, and code, etc. for the same purpose. In addition, the proposed spatial diversity scheme combines the physical-layer resources associated with the beams with other resources of the same or different protocol layers. By spatial signaling repetition to avoid Radio Link Failure (RLF) and Handover Failure (HOF), mobility robustness can be enhanced. Mission-critical and/or time-critical data delivery can also be achieved without relying on retransmission.

In one embodiment, a base station configures a plurality of control beams for data communication with a UE. The base station configures a plurality of dedicated data beams for data communication with the UE. The control beams and the dedicated data beams have different beam patterns. The base station exchanges critical data information with the UE using a first selected beam. The base station exchanges critical data information with the UE using a second selected beam.

In another embodiment, a UE established data communication with a base station via a first selected beam. The UE establishes data communication with the base station via a second selected beam. The first and the second selected beams have different beam patterns. The UE exchanges critical data information with the base station that uses the first selected beam. The UE exchanges the same critical data information with the base station that uses the second selected beam.

In a preferred embodiment, the first selected beam is a control beam and the second selected beam is a dedicated data beam. The control beam and the dedicated data beam have different beam patterns and overlapping spatial coverage. A collection of control beams covers an entire service area of a cell, and each control beam has a wider and shorter spatial coverage. A collection of dedicated data beams covers a service area of one control beam, and each dedicated data beam has a narrower and longer spatial coverage.

Other embodiments and advantages are described in the detailed description below. This summary does not purport to define the invention. The invention is defined by the claims.

BRIEF DESCRIPTION OF THE DRAWINGS

The accompanying drawings, where like numerals indicate like components, illustrate embodiments of the invention.

DETAILED DESCRIPTION

Reference will now be made in detail to some embodiments of the invention, examples of which are illustrated in the accompanying drawings.

Figure 1:
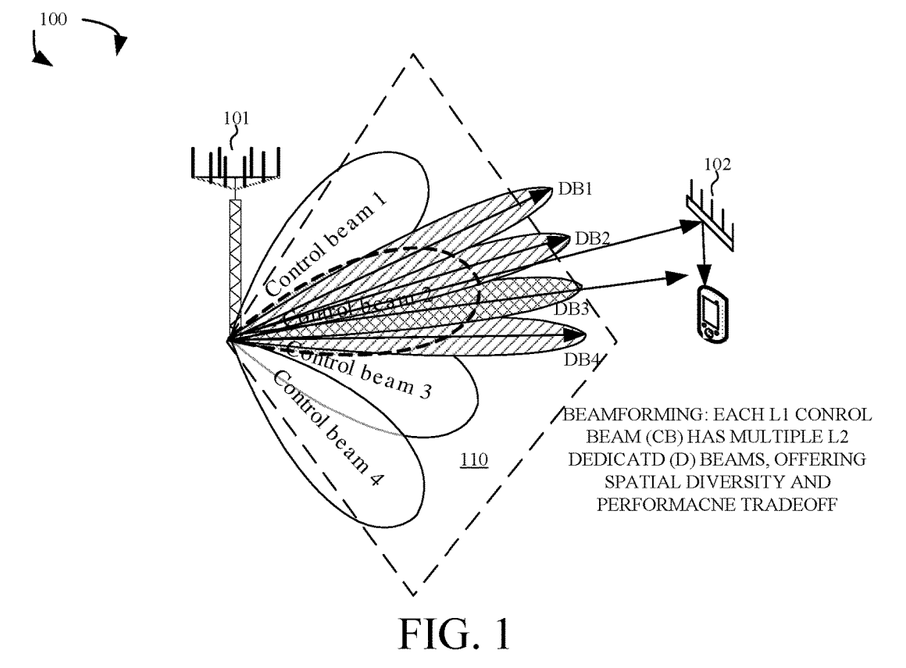
FIG. 1 illustrates multiple levels of beams for achieving spatial diversity in a beamforming mobile communication network in accordance with one novel aspect.

FIG. 1 illustrates multiple levels of beams for achieving spatial diversity in a beamforming mobile communication network 100 in accordance with one novel aspect. Beamforming mmWave mobile communication network 100 comprises a base station eNB 101 and a user equipment UE 102. In LTE systems, many handover (HO) scenarios and schemes exist, including intra macro-cell HO, intra small cell HO, and Heterogeneous Network (HetNet) and inter-system HO. In general, LTE small cell mobility can be used as the baseline for a standalone mmWave small cell. However, the heavy reliance on directional transmissions and the vulnerability of the propagation environment present particular challenges arise from channel characteristics and beamforming in mmWave small cells.

In accordance with one novel aspect, a spatial diversity scheme for enhancing the reliability and performance of data and control path in mmWave small cells is proposed. In the example of FIG. 1, eNB 101 is directionally configured with multiple cells, and each cell is covered by a set of coarse TX/RX control beams. For example, cell 110 is covered by a set of four control beams CB1, CB2, cB3, and CB4. The collection of the control beams CB1-CB4 covers an entire service area of cell 110, and each control beam has a wider and shorter spatial coverage as depicted. Each control beam in turn is covered by a set of dedicated data beams. For example, CB2 is covered by a set of four dedicated data beams DB1, DB2, DB3, and DB4. The collection of the dedicated data beams covers a service area of one control beam, and each dedicated data beam has a narrower and longer spatial coverage as depicted.

The set of control beams (CBs, also referred to as Level 1 beams or L1 beams) are lower-level control beams that provide low rate control signaling to facilitate high rate data communication on higher-level dedicated (D) data beams. Each control beam broadcasts minimum amount of cell-specific and beam-specific information similar to System Information Block (SIB) or Master Information Block (MIB) in LTE systems. The control beam and dedicated data beam architecture provides a robust control-signaling scheme to facilitate the beamforming operation in mmWave cellular network systems. Furthermore, different spatial paths offered by different levels of control beams and dedicated data beams result in different channel coherent time and fading dynamics. Multiple choices of spatial beams thus offer more spatial diversity to be explored in mmWave small cells.

The proposed spatial diversity scheme offers duplicate or incremental data/signal transmission and reception by using multiple different yet feasible beams for the same source and destination. The proposed spatial diversity scheme can be combined with other diversity schemes in time, frequency, and code, etc. for the same purpose. In addition, the proposed spatial diversity scheme combines the physical-layer resources associated with the beams with other resources (UL/DL grants, coding, RRC) of the same or different protocol layers. By spatial signaling repetition to avoid Radio Link Failure (RLF) and Handover Failure (HOF), mobility robustness can be enhanced. Mission-critical and/or time-critical data delivery can also be achieved without relying on retransmission.

Figure 2:
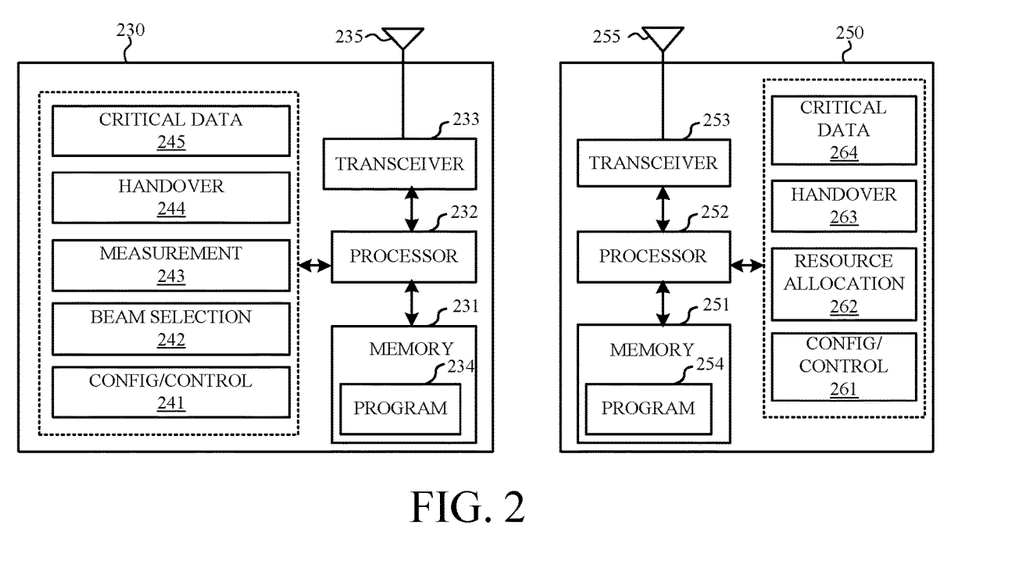
FIG. 2 is a simplified block diagram of a base station and a user equipment that carry certain embodiments of the present invention.

FIG. 2 is a simplified block diagram of a base station and a user equipment that carry certain embodiments of the present invention. UE 230 has an antenna 235, which transmits and receives radio signals. A RF transceiver module 233, coupled with the antenna, receives RF signals from antenna 235, converts them to baseband signals and sends them to processor 232. RF transceiver 233 also converts received baseband signals from processor 232, converts them to RF signals, and sends out to antenna 235. Processor 232 processes the received baseband signals and invokes different functional modules to perform features in UE 230. Memory 231 stores program instructions and data 234 to control the operations of UE 230. UE 230 also includes multiple function modules that carry out different tasks in accordance with embodiments of the current invention. A configuration and control module 241 acquires beam and measurement configuration information and establishes data communication with a base station via a selected control beam (e.g., selected by beam selection module 242), measurement module 243 performs scanning based on the beam and measurement configuration information and reports measurement report, handover module 244 performs handover from a source cell to a target cell, and critical data handling module 245 handles mission-critical and time-critical data transmission and reception by exploring spatial diversity gain.

Similarly, eNB 250 has an antenna 255, which transmits and receives radio signals. A RF transceiver module 253, coupled with the antenna, receives RF signals from antenna 255, converts them to baseband signals, and sends them to processor 252. RF transceiver 153 also converts received baseband signals from processor 252, converts them to RF signals, and sends out to antenna 255. Processor 252 processes the received baseband signals and invokes different functional modules to perform features in eNB 250. Memory 251 stores program instructions and data 254 to control the operations of eNB 250. eNB 250 also includes function modules that carry out different tasks in accordance with embodiments of the current invention. Configuration and control module 261 configures different levels of control beams and data beams for control and data transmission and measurement, resource allocation module 262 allocates resources associated with different beams and UL/DL data communication, handover module 263 performs handover based on measurement report, and critical data handling module 264 handles mission-critical and time-critical data transmission and reception by exploring spatial diversity gain.

Figure 3:
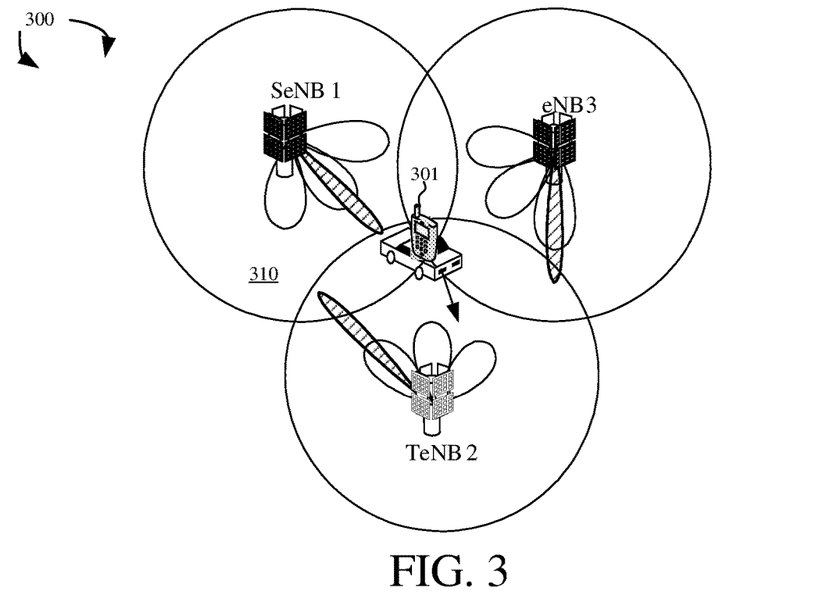
FIG. 3 illustrates multiple level of beams and spatial diversity for mobility.

FIG. 3 illustrates multiple level of beams and spatial diversity for mobility in a beamforming mmWave mobile communication network 300. Beamforming mmWave mobile communication network 300 comprises a plurality of base stations (eNBs) including a source eNodeB SeNB1, a target eNodeB TeNB2, and a neighbor eNodeB eNB3 serving a plurality of small cells. UE 301 is initially served by source base station SeNB1 in small cell 310. Later on, UE 301 may handover to target base station TeNB2 based on UE measurement report. For mobility robustness enhancement, a spatial diversity scheme can be applied by spatial repetition signaling using multiple different beams. In one example, the spatial repetition signaling is applied to mission-critical data delivery, including mobility-related signaling and data messages. The multiple different beams may be multiple control beams having different beam patterns, multiple dedicated data beams having different beam patterns, and/or a combination of different levels of control beam and dedicated data beam having different beam patterns. In addition to mobility enhancement, the spatial repletion signaling can also be applied to time-critical data delivery, including voice and video associated with high priority applications. Another example of critical data information is reference signals, sounding signals, or pilot signals.

Figure 4:
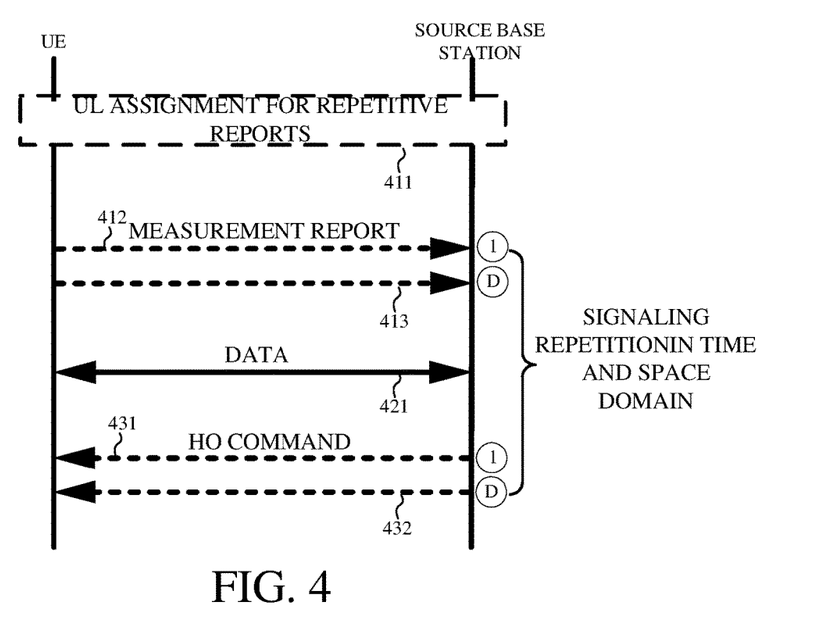
FIG. 4 is a signaling flow chart of supporting spatial diversity for critical data delivery.

FIG. 4 is a signaling flow chart of supporting spatial diversity for critical data delivery during a handover procedure. In step 411, a UE receives an uplink (UL) assignment for sending repetitive measurement reports from a source base station. In step 412, the UE sends the measurement report to the base station that uses a first beam (e.g., a Level 1 control beam). In step 413, the UE sends the same measurement report to the base station that uses a second beam (e.g., a dedicated data beam). In step 421, the UE and the base station continue to exchange UE data. In step 431, the base station determines to handover the UE to another target base station and transmits a handover command to the UE using a first beam (e.g., a level 1 control beam). In step 432, the base station transmits the same handover command to the UE using a second beam (e.g., a dedicated data beam). Both measurement report and handover command are mission-critical data related to mobility management. By providing spatial signaling repetition using multiple beams, unnecessary RLF and HOF can be avoided, without performing retransmission or waiting for ACK/NACK from the peer device to perform retransmission.

Figure 5:
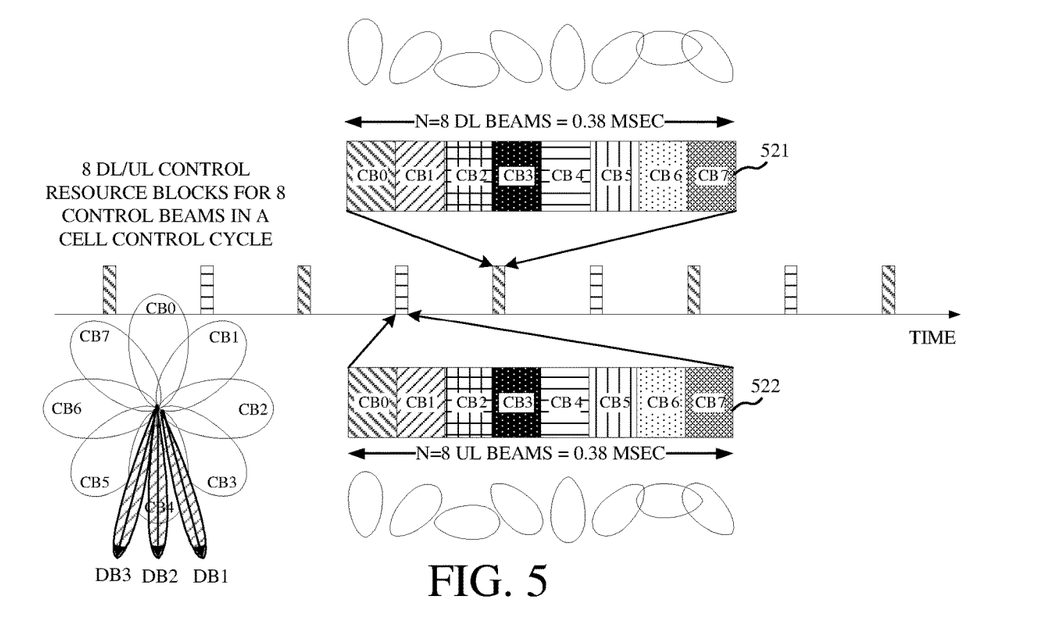
FIG. 5 illustrates an example of multilevel beams in each standalone mmWave small cell.

FIG. 5 illustrates an example of multilevel beams in each standalone mmWave small cell. In each standalone mmWave small cell, multiple levels of beams exist, with multiple beam patterns per level. A base station is directionally configured with multiple cells, and each cell is covered by a set of coarse TX/RX control beams. In one embodiment, a serving cell is covered by eight control beams CB0 to CB7. Each control beam comprises a set of downlink resource blocks, a set of uplink resource blocks, and a set of associated beamforming weights with moderate beamforming gain. In the example of FIG. 5, different periodically configured control beams are time division multiplexed (TDM) in time domain. A downlink subframe 521 has eight DL control beams occupying a total of 0.38 msec. An uplink subframe 522 has eight UL control beams occupying a total of 0.38 msec. The interval between the DL subframe and the UL subframe is 2.5 msec. The set of control beams are lower-level control beams (also named Level 1 beams or L1 beams) that provide low rate control signaling to facilitate high rate data communication on higher-level dedicated (D) data beams.

Each control beam in turn is covered by a set of dedicated data beams. For example, CB4 is covered by a set of four dedicated data beams DB1, DB2, DB3, and each data beam has a different beam pattern. Note that for each CB, it has overlapping spatial coverage with the corresponding multiple dedicated data beams. Despite the names, the different levels of beams are not limited to either data or control. Different spatial paths offered by different levels of control beams and dedicated data beams result in different channel coherent time and fading dynamics. Multiple choices of spatial beams thus offer more spatial diversity to explore in mmWave small cells.

In one example, the spatial diversity can be achieved by spatial repetition signaling applied to critical data delivery using multiple levels of beams. A critical data is first transmitted or received via an L1 control beam, and the same critical data is then transmitted or received via a dedicated data beam within the L1 control beam. The control beam and the data beam have overlapping spatial coverage but different beam patterns. In another example, the spatial diversity can be achieved by spatial repetition signaling applied to critical data delivery using the same level of beams having different beam patterns. If a UE is located in between two control beams, then the two different control beams may be used for the critical data delivery to explore spatial diversity and improve robustness.

Figure 6:
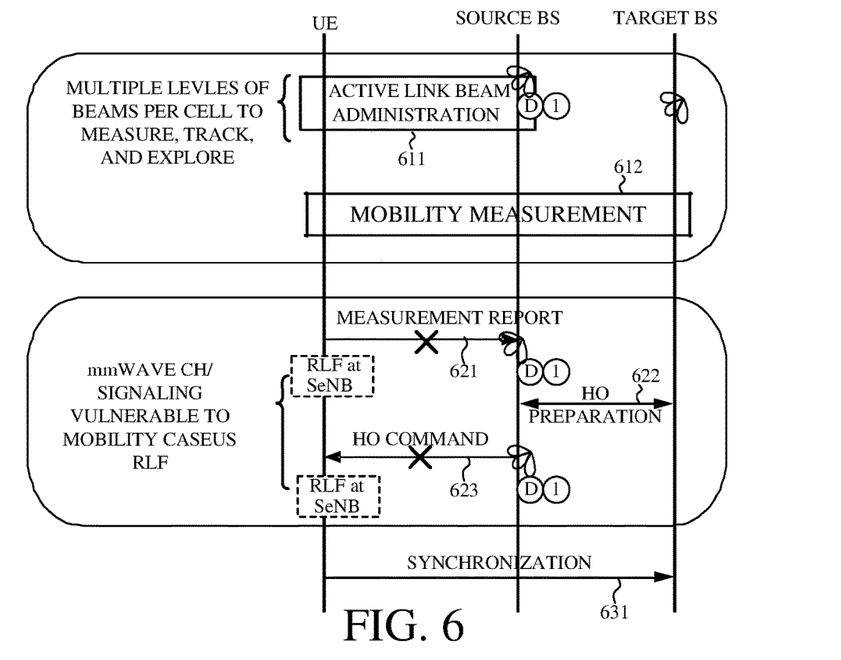
FIG. 6 illustrates an example of critical data delivery in beamformed mmWave small cell mobility.

FIG. 6 illustrates an example of critical data delivery in beamformed mmWave small cell mobility. In the example of FIG. 6, a UE is served by a source base station and later on the UE handovers to a target base station. In step 611, the UE and the source base station performs active link beam administration. The active link beam administration involves configuring multiple levels of beams per cell for UE to measure, track, and explore spatial diversity. In step 612, the UE performs radio signal measurements over the configured multiple levels of beams of the serving cell as well as neighboring cells of the target base station. In step 621, the UE sends a measurement report to the source base station. In step 622, the source base station makes handover decision based on the measurement report and performs HO preparation with the target base station. In step 623, the source base station sends an HO command to the UE. Finally, in step 631, the UE performs synchronization with the target base station upon receiving the HO command and handovers to the target base station.

Due to vulnerable mmWave beamformed channel in mobility, more link outage, more frequency RLF, and more HO failure are possible. First, mmWave channel coherent time and stable spatial path's lifetime is expected one order of magnitude shorter than traditional cellular bands due to wavelength difference. Second, the number of effective transmission paths for a beam could be rather limited, thus more vulnerable to UE movement and environmental changes. In normal operation, regardless of mobility or not, due to the uncertainty in beam tracking and alignment, time-critical data loss at a specific beam level may not be sufficiently delivered by HARQ ACK/NACK/Re-TX, or even by a single level of beam.

Possible causes of handover failure in radio interference are measurement report failure (in step 621) and HO command transmission failure (in step 623) due to channel degradation. As a result, RLF is triggered for connection re-establishment. Furthermore, geographic location and uncertainty in beam level selection during the HO transition period causes link disruption and data loss. For control beam, it is more reliable but of poorer coverage to cell edge users. For dedicated data beam, it offers better link budget but more sensitive to direction (moving) changes. To improve the data delivery success rate, particularly of mission-critical or time-critical data, spatial transmission diversity in combination with multiple resource dimensions is proposed to explore the diversity at multiple protocol layers for different application scenarios.

Figure 7:
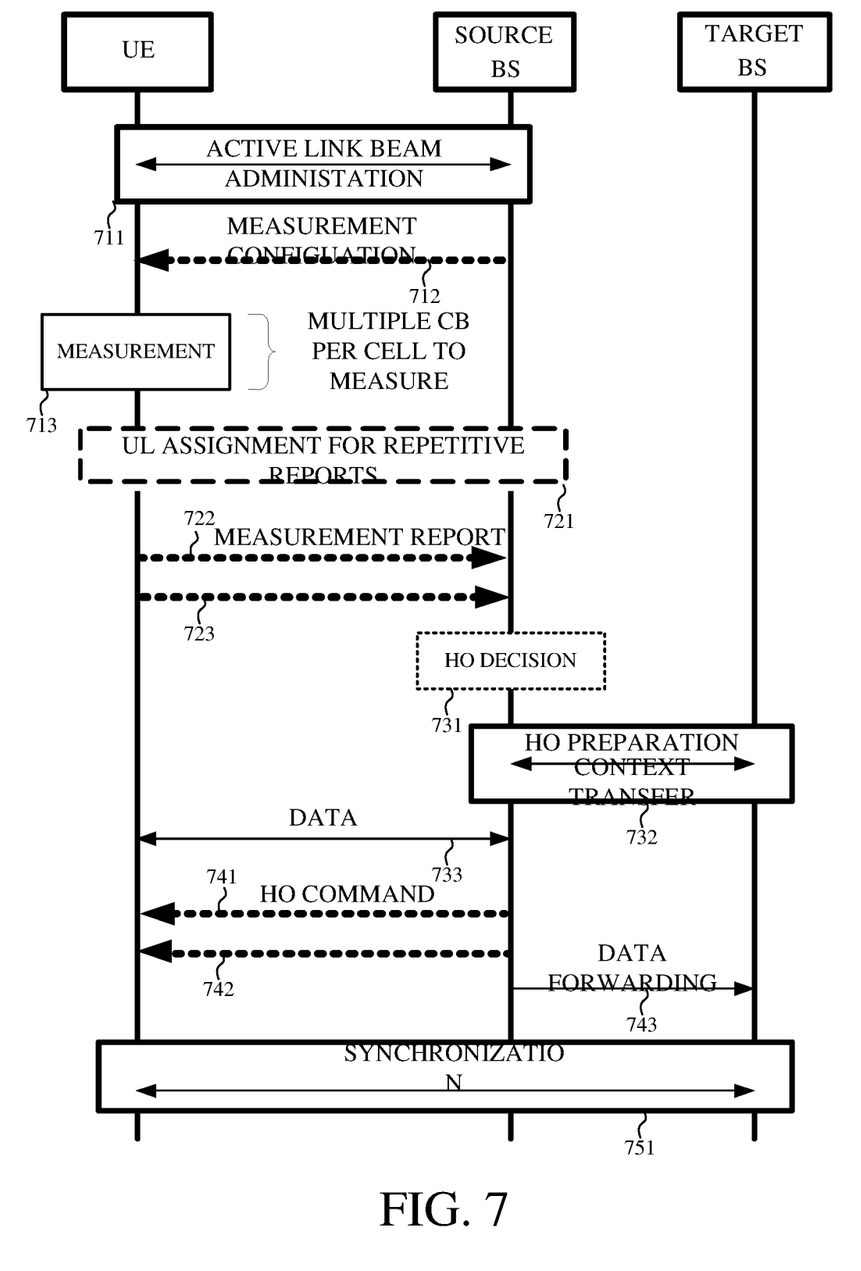
FIG. 7 illustrates one embodiment of spatial diversity for critical data delivery in beamformed mmWave small cell mobility.

FIG. 7 illustrates one embodiment of spatial diversity for critical data delivery in beamformed mmWave small cell mobility. In the example of FIG. 7, a UE is served by a source base station and later on the UE handovers to a target base station. In step 711, the UE and the source base station performs active link beam administration. The active link beam administration involves configuring multiple levels of beams per cell for UE to measure, track, and explore spatial diversity. In step 712, the UE receives measurement configuration for different beam measurement in different cells. In step 713, the UE performs radio signal measurements over the configured multiple levels of beams of the serving cell as well as neighboring cells of the target base station based on the measurement configuration.

In step 721, the UE receives multiple UL grants for sending repetitive measurement reports from the source base station. The multiple UL grants should be bundled so that the UE knows the grants are for the same UL data. In step 722, the UE sends the measurement report to the source base station that uses a first beam (e.g., a Level 1 L1 control beam). In step 723, the UE sends the same measurement report to the source base station that uses a second beam (e.g., a dedicated data beam). In step 731, the source base station determines to handover the UE to the target base station based on the measurement report. In step 732, the source base station and the target base station performs handover preparation. In step 733, the UE and the source base station continues to exchange UE data. In step 741, the source base station transmits a handover command to the UE using a first beam (e.g., a Level 1 L1 control beam). In step 742, the source base station transmits the same handover command to the UE using a second beam (e.g., a dedicated data beam). In step 743, the source base station forwards the UE data to the target base station. Finally, in step 751, the UE performs time and frequency synchronization with the target base station and handovers to the target base station.

Using the above HO signaling as an example, additional beam space domain is utilized for spatial diversity of critical data delivery. The base station utilizes different beamforming weights for duplicate signaling and data transmission (TX). The different beamforming weights may experience different transmission paths, and thus different channel conditions, that offers diversity for the UE to explore. The same method can be used for BS receiving (RX), or for mixed RX and TX, or for UE RX/TX as well.

In one embodiment, the signaling diversity is achieved in beam space and time domain. At BS, a desired signaling is first transmitted at time=t1 with a selected beam (e.g., HO command in step 741). At BS, a duplicated signaling is transmitted at time=t2 with another selected beam (e.g., HO command in step 742). The two selected beams are preferably different, and the transmission frequency resource may be the same. Note that the time-t2 transmission is not necessarily after the time-t1 transmission is acknowledged by the receiver, in contrast to what HARQ mandates.

In another embodiment, the signaling diversity is achieved in beam space and frequency domain. As BS, a desired signaling is transmitted with a selected beam, on frequency resources f1. At BS, a duplicated signaling is transmitted with another selected beam, on frequency resources f2. The two selected beams are preferably different, and the transmission timing of the two signaling may be the same. Note that the other direction of transmission and reception can be performed similarly to achieve spatial diversity.

In yet another embodiment, the signaling diversity in a combination of beam space, time domain, and frequency domain can be explored by enhancing the HARQ process. For example, a single RRC signaling message can be transmitted once at upper layer while physical layer tries different diversity combinations implicitly. The duplicate signaling can be different redundancy versions in HARQ process of the same packet. For example, control beam can be used for low-modulation meta-data of some message to deliver, while dedicated beam used for high-modulation delivery of refined-data of the same message, analog to incremental redundancy or incremental video encoding. The receiver of the data over control and dedicated beams exploits both the energy gain and the coding gain.

Cross-layer processing of duplication may also be applied to achieve diversity. For example, multiple MAC/RRC layer messages of duplicate content can be transmitted explicitly at different timing without waiting for ACK/NACK from the receiver, i.e., with MAC-layer explicit duplicate resource assignments. With MAC/RRC layer instruction, physical layer tries different diversity for transmitting each duplicate. At the receiver, physical layer may pursue some post-processing, e.g., coherent combinations or any ACK/NACK discarding, of duplicates from different beam-space diversity. Note that the PHY-layer post-processing of the duplicate transmissions may need explicit signaling between the transmitter and the receiver. Alternatively, at the receiver, PHY-layer may forward the received duplicate to upper layers for some post process without the need of cross-layer instructions between MAC/RRC and PHY layers.

Figure 8:
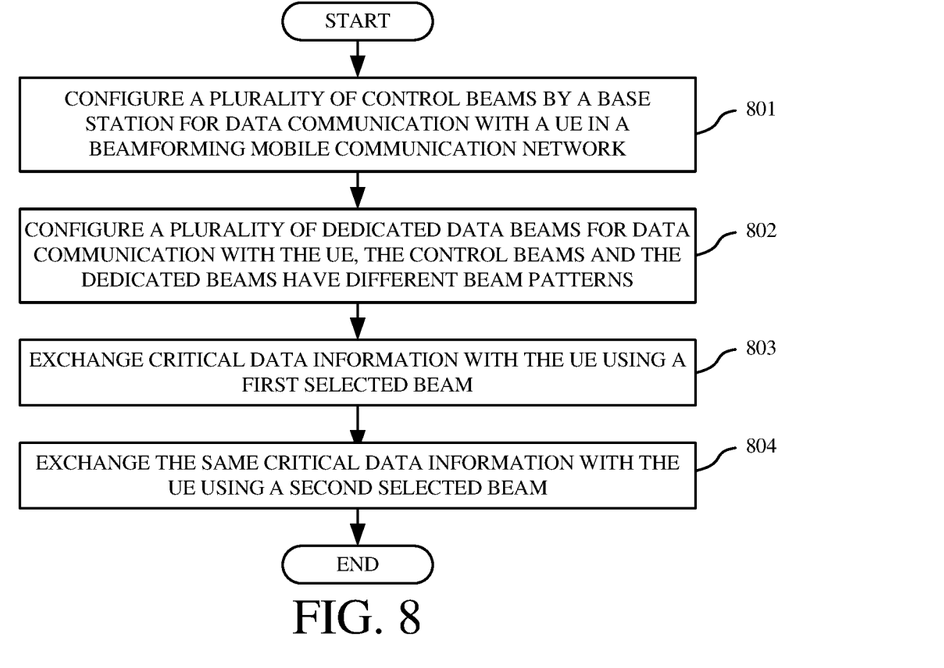
FIG. 8 is a flow chart of a method of providing spatial diversity for critical data delivery from base station perspective, in a beamformed mmWave small cell in accordance with one novel aspect.

FIG. 8 is a flow chart of a method of providing spatial diversity for critical data delivery from base station perspective, in a beamformed mmWave small cell in accordance with one novel aspect. In step 801, a base station configures a plurality of control beams for data communication with a UE. In step 802, the base station configures a plurality of dedicated data beams for data communication with the UE. The control beams and the dedicated data beams have different beam patterns. In step 803, the base station exchanges critical data information with the UE using a first selected beam. In step 804, the base station exchanges critical data information with the UE using a second selected beam.

Figure 9:
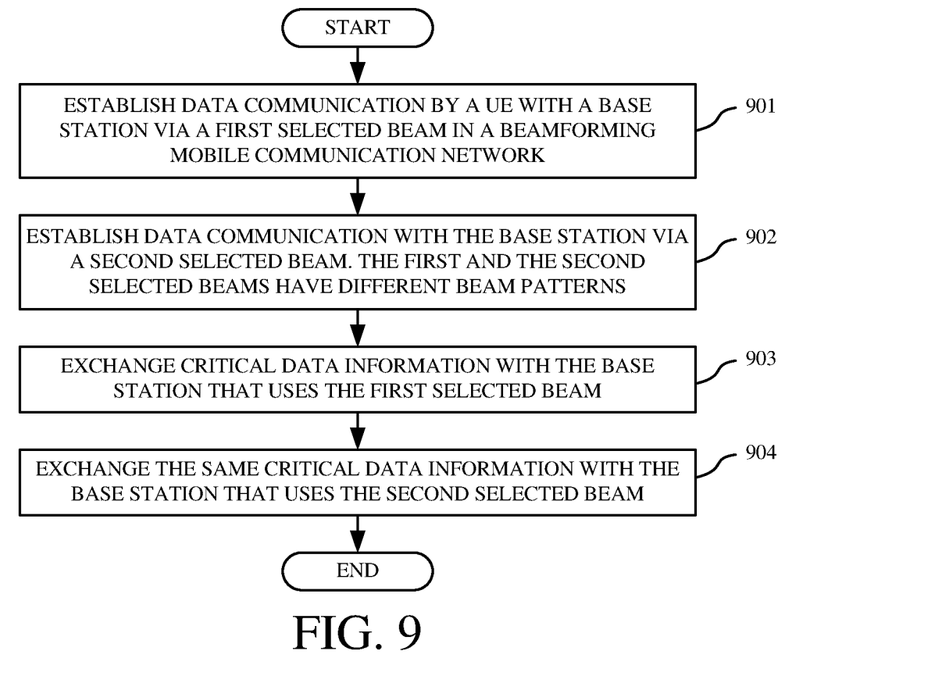
FIG. 9 is a flow chart of a method of providing spatial diversity for critical data delivery from user equipment perspective, in a beamformed mmWave small cell in accordance with one novel aspect.

FIG. 9 is a flow chart of a method of providing spatial diversity for critical data delivery from user equipment perspective, in a beamformed mmWave small cell in accordance with one novel aspect. In step 901, a UE established data communication with a base station via a first selected beam. In step 902, the UE establishes data communication with the base station via a second selected beam. The first and the second selected beams have different beam patterns. In step 903, the UE exchanges critical data information with the base station that uses the first selected beam. In step 904, the UE exchanges the same critical data information with the base station that uses the second selected beam.

For DL transmission, there can be multiple different methods to exploit the proposed spatial diversity in beam space. For example, the BS transmits the same RLC PDU with the same method, i.e., different beam levels. The UE receives the transmissions as independent transmissions. At RLC layer, duplicate reception is discarded. Likewise, for UL transmission, the BS may give multiple UL grants for the same UE payload. The multiple UL grants should be bundled so that UE knows the grants are for the said method. The UE is aware of what kind of payload such method shall be applied. The UE transmits the same traffic of the payload type on the multiple UL grants. The BS receives the transmission with different beam levels and does coherent combination.

Although the present invention has been described in connection with certain specific embodiments for instructional purposes, the present invention is not limited thereto. Accordingly, various modifications, adaptations, and combinations of various features of the described embodiments can be practiced without departing from the scope of the invention as set forth in the claims.

The invention claimed is:

1. A reaction product comprising one or more diamines comprising primary or secondary amine moieties with a reaction product comprising one or more monoamines comprising primary or secondary amine moieties and one or more compounds having formula:

(I)

where R is a linking group having formula:

(II)

(III)

(IV)

(V)

where $R_1$, $R_2$ may be the same or different and comprise hydrogen, linear or branched $(C_1-C_4)$alkyl, hydroxyl, hydroxy$(C_1-C_3)$alkyl, carboxyl, carboxy$(C_1-C_3)$alkyl or $(C_1-C_3)$alkoxy; and m is an integer of 1 to 15, wherein the one or more diamines comprises a formula:

(XX)

where R" is a linking group and $R_{42}$ and $R_{43}$ may be the same or different and comprise hydrogen, linear or branched $(C_1-C_{12})$alkyl, alkyleneoxy or substituted or unsubstituted $(C_6-C_{18})$aryl, wherein R" comprises:

(XXI)

(XXII)

(XXIII)

(XXIV)

(XXV)

or a substituted or unsubstituted $(C_6-C_{18})$aryl; where $R_{44}$-$R_{51}$ may be the same or different and comprise hydrogen, linear or branched $(C_1-C_5)$alkyl, linear or branched hydroxy$(C_1-C_5)$alkyl or linear or branched $(C_1-C_5)$alkoxy; and Z is a carbon atom or nitrogen atom; and p and t may be the same or different and are independently integers of one or greater, e is an integer of 0 to 3, and a, b, c and d may be the same or different and are numbers from 1 or greater.

* * * * *